United States Patent [19]
Arieff et al.

[11] Patent Number: 6,010,454
[45] Date of Patent: Jan. 4, 2000

[54] FLUID AND ELECTROLYTE BALANCE MONITORING SYSTEM FOR SURGICAL AND CRITICALLY ILL PATIENTS

[75] Inventors: Allen I. Arieff, Sausalito; Roger A. Stern, Cupertino, both of Calif.

[73] Assignee: Aquintel, Inc., Mountain View, Calif.

[21] Appl. No.: 08/965,549

[22] Filed: Nov. 6, 1997

Related U.S. Application Data

[60] Provisional application No. 60/047,923, May 29, 1997.
[51] Int. Cl.⁷ .................................................. A61B 5/00
[52] U.S. Cl. ........................ 600/309; 600/573; 600/584
[58] Field of Search ................................ 600/309, 573, 600/579, 581, 584, 578; 604/27–30, 65–67, 317, 318, 322

[56] References Cited

U.S. PATENT DOCUMENTS

| | | | |
|---|---|---|---|
| 4,448,207 | 5/1984 | Parrish | 128/771 |
| 4,449,538 | 5/1984 | Corbitt et al. | 128/760 |
| 4,531,088 | 7/1985 | Czaban et al. | 324/71.1 |
| 4,658,834 | 4/1987 | Blankenship et al. | 128/771 |
| 4,709,331 | 11/1987 | Barkett et al. | 364/413 |
| 4,743,352 | 5/1988 | Watkins-Pitchford | 204/406 |
| 4,773,423 | 9/1988 | Hakky | 128/637 |
| 4,869,266 | 9/1989 | Taylor et al. | 128/774 |
| 4,871,439 | 10/1989 | Enzer et al. | 204/401 |
| 4,922,922 | 5/1990 | Pollock et al. | 600/573 |
| 4,923,613 | 5/1990 | Chevallet | 210/647 |
| 4,946,651 | 8/1990 | Liston et al. | 422/102 |
| 5,001,067 | 3/1991 | Coleman et al. | 436/63 |
| 5,029,584 | 7/1991 | Smith | 128/638 |
| 5,100,554 | 3/1992 | Polaschegg | 210/647 |
| 5,109,850 | 5/1992 | Blanco et al. | 128/635 |
| 5,112,622 | 5/1992 | Kopp | 424/663 |
| 5,120,422 | 6/1992 | Liu et al. | 204/416 |
| 5,200,345 | 4/1993 | Young | 436/63 |
| 5,200,627 | 4/1993 | Chevallet | 250/573 |

(List continued on next page.)

OTHER PUBLICATIONS

Sheppard, Kouchoukos, and Kirklin; The Digital Computer in Surgical Intensive Care Automation; Jul. 1973; pp. 29–34.

Sheppard and Kirklin; Cardiac surgical intensive care computer system; Federation Proceedings vol. 33, No. 12; circa 1977; pp. 2326–2328.

Sheppard, Kouchoukos, Kurtis, and Kirklin; Automated Treatment of Critically III Patients Following Operation; Annals of Surgery; Oct. 1968; pp. 596–604.

Sheppard and Kouchoukos; Automation of measurements and interventions in the systematic care of postoperative cardiac surgical patients; Medical Instrumentation; Sep.–Oct. 1977; pp. 296–301.

Bowman and Westenskow; A Microcomputer–Based Fluid Infusion System for the Resuscitation of Burn Patients; IEEE Transactions on Biomedical Engineering, vol. BME–28, No. 6; Jun. 1981; pp. 475–479.

Westenskow; Automating Patient Care with Closed–Loop Control; M.D. Computing; 1986; pp. 14–20.

*Primary Examiner*—Eric F. Winakur
*Attorney, Agent, or Firm*—Carr & Ferrell LLP

[57] ABSTRACT

A computer based system for tracking a patient's fluid volume and electrolyte (cation or anion concentration) balances, during the period extending from before surgical procedures through the recovery process, which will assist the attending physician in maintaining proper balances in the patient. The system contains automatic sensors for measuring the volumes of fluids administered to and recovered from the patient. The system also preferably contains sensors for measuring electrolyte concentrations in these fluids, and, when sensors are not available, assists the attending physician in estimating. The system assists the attending physician in creating baseline values for a patient's fluid and electrolyte values, and then accounts for the fluids going into and out of the patient to continuously track current values. Out of bounds conditions for these balances, when detected, will cause the system to issue alarms and make suggestions to the attending physician for remedial action.

29 Claims, 11 Drawing Sheets

U.S. PATENT DOCUMENTS

| | | | |
|---|---|---|---|
| 5,226,313 | 7/1993 | Murata et al. | 73/149 |
| 5,236,664 | 8/1993 | Ludvigsen | 422/44 |
| 5,285,682 | 2/1994 | Micklish | 73/149 |
| 5,331,958 | 7/1994 | Oppenheimer | 128/633 |
| 5,395,321 | 3/1995 | Kawahara et al. | 604/67 |
| 5,415,176 | 5/1995 | Sato et al. | 128/734 |
| 5,437,629 | 8/1995 | Goldrath | 604/21 |
| 5,492,537 | 2/1996 | Vancaillie | 604/246 |
| 5,503,626 | 4/1996 | Goldrath | 604/65 |
| 5,522,805 | 6/1996 | Vancaillie et al. | 604/246 |
| 5,611,351 | 3/1997 | Sato et al. | 128/734 |

COMPOSITION OF IV FLUIDS

| Type of IV Fluid | Sodium mmol/L | Potassium mmol/L | Chloride mmol/L | Bicarbonate mmol/L | Glucose mmol/L | Common Name |
|---|---|---|---|---|---|---|
| Normal saline | 154 | 0 | 154 | 0 | 0 | NS |
| Half-normal saline | 77 | 0 | 77 | 0 | 0 | ½ NS |
| 5% dextrose in water | 0 | 0 | 0 | 0 | 280 | D5/W |
| 3% hypertonic saline | 514 | 0 | 514 | 0 | 0 | hypertonic Saline |
| Ringers lactate | 130 | 4 | 112 | 28 | 0 | RL |
| 5% dextrose in saline | 154 | 0 | 154 | 0 | 280 | D5/NS |
| 5% dextrose in Ringers lactate | 130 | 4 | 112 | 28 | 280 | D5/RL |
| 5% sodium bicarbonate | 595 | 0 | 0 | 595 | 0 | |
| Blood plasma | 140 | 4 | 105 | 26 | 6 | |
| Whole blood | 140 | 4 | 105 | 26 | 6 | |
| Blood fractions (platelets, clotting factors, fibrinogen) | 0 | 0 | 0 | 0 | 0 | |

FIG. 7

ELECTROLYTE CONTENT OF BODY FLUIDS

Mean concentration (mmol/liter) followed by normal ranges of four predominant electrolytes

| Fluid | | Na+ | K+ | Cl- | HCO3- |
|---|---|---|---|---|---|
| Plasma | Mean value | 140 | 4.5 | 102 | 26 |
| | Range | 137-142 | 3.5-5.0 | 99-104 | 23-28 |
| Saliva | Mean value | 33 | 20 | 34 | |
| | Range | 20-46 | 16-23 | 24-44 | |
| Gastric juice | Mean value | 60 | 9 | 84 | 0 |
| | Range | 30-90 | 4.3-12 | 52-124 | |
| Bile | Mean value | 149 | 4.9 | 101 | 45 |
| | Range | 120-170 | 3-12 | 80-120 | 30-50 |
| Pancreatic juice | Mean value | 141 | 4.6 | 77 | 92 |
| | Range | 113-153 | 2.6-7.4 | 54-95 | 70-110 |
| Small bowel | Mean value | 105 | 5.1 | 99 | 50 |
| | Range | 72-158 | 3.5-6.8 | 70-127 | 20-40 |
| Ileal fluid | Mean value | 129 | 11.2 | 116 | 29 |
| | Range | 90-140 | 6-30 | 82-125 | 25-30 |
| Cecal fluid | Mean value | 80 | 21 | 48 | 22 |
| | Range | 50-116 | 11-28 | 35-70 | 15-30 |
| Cerebrospinal fluid | Mean value | 141 | 2.9 | 127 | 23 |
| | Range | 135-147 | 2.5-3.4 | 116-132 | 21-25 |
| Perspiration | Mean value | 45 | 4.5 | 58 | 0 |
| | Range | 18-97 | 2.0-10 | 18-97 | |

FIG. 8

AQUINTEL™ I/Ometer

PATIENT 123456

| SEX | AGE | HEIGHT | WEIGHT | BMI | TBW | TBC |
|-----|-----|--------|--------|-----|-----|-----|
| F | 30 | 5' 2" | 127 lbs | 23.3 | 28 L | 3864 mmol |

FLUIDS ADMINISTERED

| FLUID | VOLUME | CATION CONCENTRATION | CUMULATIVE TBW | TOTAL CATION CHANGE |
|-------|--------|----------------------|----------------|---------------------|
| ➢ RINGERS | + 4000 mL | + 133 mmol/L | + 32000 mL | + 532 mmol |
| DEXTROSE | + 2000 mL | + 0 mmol/L | + 34000 mL | + 0 mmol |
| CHANGE | + 6000 mL | | | + 532 mmol |

FLUIDS COLLECTED

| FLUID | VOLUME | CATION CONCENTRATION | CUMULATIVE TBW | TOTAL CATION CHANGE |
|-------|--------|----------------------|----------------|---------------------|
| ➢ URINE | - 3100 mL | - 75 mmol/L | + 30900 mL | - 233 mmol |
| ➢ GASTRIC CHEST BILIARY | - 3600 mL | - 120 mmol/L | + 27300 mL | - 432 mmol |
| BLOOD EMESIS DIARRHEA | - 1800 mL | - 140 mmol | + 25500 mL | - 252 mmol |
| CHANGE | - 8500 mL | | | - 917 mmol |

NET FLUID AND ELECTROLYTE BALANCE

| VOLUME | CATION CONCENTRATION | CUMULATIVE TBW | TOTAL CATION CHANGE |
|--------|----------------------|----------------|---------------------|
| - 2500 mL | 136 mmol/L | + 25500 mL | - 385 mmol |

*FIG. 9*

| | total body water, liters, running total | gains | losses | source | total body cation, mmoles, running total | gains | losses | source | cation concentration mmol/L |
|---|---|---|---|---|---|---|---|---|---|
| pre-op | 28 liters | | | | 3864 | | | | |
| during surgery | 32 | 4 | | Ringers lactate | 4396 | 532 | | Ringers lactate | 133 |
| during surgery | 30.2 | | 1.8 | blood loss | 4144 | | 252 | blood loss | 140 |
| after surgery | 30.2 | | | | 4144 | | | | |
| | 26.6 | | 3.6 | gastric suction | 3712 | | 432 | gastric suction | 120 |
| | 23.5 | | 3.1 | urine | 3480 | | 232 | urine | 75 |
| | 25.5 | 2 | | IV 5% dextrose | 3480 | 0 | | | 0 |
| net water deficit | 2.5 liters | | | | | | | | |
| net cation deficit | | | | | 384 mmoles | | | | |
| post op balance | 25.5 liters | | | | 3480 mmoles | | | | |

*FIG. 11*

FLUID AND ELECTROLYTE BALANCE MONITORING SYSTEM FOR SURGICAL AND CRITICALLY ILL PATIENTS

CROSS-REFERENCE TO RELATED APPLICATION

The present application claims under 35 U.S.C. § 119(e) the benefit of the filing date of provisional application Ser. No. 60/047,923 which was filed on May 29, 1997.

BACKGROUND OF THE INVENTION

1. Field of the Invention

The present invention relates generally to patient monitoring systems and more specifically to patient fluid monitoring systems.

2. Discussion of the Prior Art

Human patients undergoing surgery lose fluids which require replacement at rates depending upon the location and type of surgery. Peripheral procedures require the least fluids while intra-abdominal procedures require the most. Some procedures even introduce more fluid into patients than is removed. Procedures such as transurethral bladder and prostate resections, and hysteroscopic vaginal hysterectomies using large volumes of irrigating solutions may result in absorption of significant amounts of the irrigating solution accompanied by increased intravascular volume and the dangers of congestive heart failure and hyponatremia (see J. C. Ayus & A. I. Arieff, *Glycine-induced Hypoosmolar Hyponatremia*, 157 Arch. Intern. Med. 223 (1997), which is hereby incorporated by reference).

Much of the rationale for administering large quantities of postoperative fluids, despite the attendant dangers of pulmonary edema, include the effects of the "third space," regions in the body occupied by fluids which are not in equilibrium with the bloodstream. Examples of the third space include burns, bruises, traumatized operative bed (intra-abdominal or intra-thoracic), traumatically injured tissues, and infarcted tissues. Fluids in the third space are literally out of circulation and therefore hemodynamically inactive. Fluid sequestration in the third space is a unique kind of fluid loss in postoperative patients (see M. H. Rosenthal & A. I. Arieff, *Fluid and Electrolyte Therapy in Critically Ill Patients and Those Who Are Pre-, Post-, or Intraoperative*, in Fluid, Electrolyte and Acid-Base Disorders 597 (A. I. Arieff & R. A. DeFronzo eds., 1995), which is hereby incorporated by reference).

However, there is no simple bedside method for accurately measuring these fluid losses, and in actual practice clinical approximation determines replacement. The sequestered extracellular fluid (third space losses) postoperatively during an uncomplicated procedure varies between negligible and 3 liters. Quantification of functional extracellular fluid using the available means of measuring is extremely difficult, and consequently no accurate a priori formula for intraoperative fluid administration has been derived.

Postoperative fluid balance depends on underlying pathology factors including anesthesia, intraoperative fluid therapy and intra- and post-operative complications. Humoral mediators (such as the renin-angiotensin system, catecholamines, aldosterone, and AVP), which can influence hemodynamics and are released during surgery as described below, may persist into the postoperative period and require continuous administration of large volumes of fluids. While the intravascular volume must be maintained to avoid postoperative renal insufficiency, too much postoperative fluid can result in heart and lung failure with pulmonary edema. The potential postoperative complication of pulmonary edema and respiratory failure is a major hazard which discourages administering fluids in sufficient quantities to maintain preload.

The quantity of fluid necessary to induce pulmonary edema varies according to individual patient factors such as age, body weight, tissue turgor, cardiac function, pulmonary function, renal function, plasma vasopressin levels, and plasma proteins. The literature includes some information concerning minimal quantities of fluid which could induce pulmonary edema in otherwise generally healthy postoperative patients, but this information does not imply that any given quantity of fluid will necessarily induce pulmonary edema. Little information is available concerning the maximum postoperative volume of fluid which can be safely administered. In particular, it is not clear what volume of fluid might result in pulmonary edema in a postoperative patient who does not have serious cardiovascular, hepatic or renal disorders.

FIG. 1 is a bar chart illustrating the incidence of pulmonary edema among a total of 161 patients who retained an average of 2.2 liters of fluid per day following surgery.

Postoperative hyponatremia is the most frequent postoperative electrolyte complication among adults in the United States and in the United Kingdom. Every post operative patient should be considered at risk to develop hyponatremia. (see C. L. Fraser & A. I. Arieff, *Epidemiology, Pathophysiology, and Management of Hyponatremic Encephalopathy*, 102 Am. J. Med. 67 (1997); R. Zerbe & G. Robertson, *Osmotic and Nonosmotic Regulation of Thirst and Vasopressin Secretion*, in Clinical Disorders of Fluid and Electrolyte Metabolism 81 (R. G. Narins ed., 1994); A. I Arieff, J. C. Ayus, & C. L. Fraser, *Hyponatremia and Death or Permanent Brain Damage in Healthy Children*, 304 Brit. Med. J. 1218 (1992); and J. C. Ayus, J. M. Wheeler, & A. I. Arieff, *Postoperative Hyponatremic Encephalopathy in Menstruant Women*, 117 Ann. Intern. Med. 891 (1992), which are hereby incorporated by reference).

FIG. 2 shows that, among the approximately 25 million annual inpatient surgeries per year in the United States, an incidence of about 1% of postoperative hyponatremia results in about 250,000 cases per year. It has recently been projected that of postoperative patients who develop hyponatremic encephalopathy about 25% (above 12,000 per year in the USA) eventually die or suffer permanent brain damage. (see J. C. Ayus & A. I. Arieff, *Brain Damage and Postoperative Hyponatremia: Role of Gender*, 46 Neurology 323 (1996), which is hereby incorporated by reference).

The incidence of hypernatremia among all hospitalized patients is about 1.5% (375,000 patients) and about 21% of this total are postoperative (about 80,000 patients). If only isotonic fluids (154 mmol/L NaCl) are administered to postoperative patients, hypernatremia may develop (see N. A. Snyder & A. I. Arieff, *Neurological Manifestations of Hypernatremia*, in Metabolic Brain Dysfunction in Systematic Disorders 87 (R. A. Griggs & A. I. Arieff, eds., 1992), which is hereby incorporated by reference). In postoperative patients, hypernatremia is caused by a relative lack of free water, and is associated with a mortality rate in excess of 40% (about 40,000 deaths) as shown in FIG. 3 (Id.; see also P. M. Palevsky, R. Bhagrath, & A. Greenberg, *Hypernatremia in Hospitalized Patients*, 124 Ann. Intern. Med. 197 (1996), which is hereby incorporated by reference).

Thus, as shown in FIG. 4, three major postoperative complications, hypernatremia, hyponatremia, and pulmonary edema affect almost 650,000 postoperative patients, with an estimated mortality of 78,000 individuals, per year in the USA (see M. H. Rosenthal & A. I. Arieff, *Fluid and Electrolyte Therapy in Critically Ill Patients and Those Who Are Pre-, Post-, or Intraoperative,* in Fluid, Electrolyte and Acid-Base Disorders 597–632 (A. I. Arieff & R. A. DeFronzo eds., Churchill Livingstone, New York, 1995).

The art related to the field of systematic monitoring of the fluid and electrolyte balances in patients includes partial solutions to the above-described problems. There is no prior art comprehending a systematic approach which can warn physicians when a major problem (hyponatremia, hypernatremia, pulmonary edema) is imminent, and give meaningful suggestions to an attending physician. In many hospitals' operating rooms the fluid input and output volumes are roughly estimated by an attending physician aided only by his or her visual observations and experience.

Among prior inventions directed towards certain aspects of the fluid and electrolyte balance problem, Parrish (U.S. Pat. No. 4,448,207) and Blankenship, et al. (U.S. Pat. No. 4,658,834) both disclose apparatuses using sonic transducers for measuring of the volume of fluids outgoing from a patient. Corbitt, et al. (U.S. Pat. No. 4,449,538) discloses an apparatus which measures bulk fluid input and output volumes and advises an attending physician, but not on electrolyte balance. Cormier, et al. (U.S. Pat. No. 4,531,088) discloses in-line blood analysis through electrical resistance measuring, and Oppenheimer (U.S. Pat. No. 5,331,958) does the same through laser beams. Micklish (U.S. Pat. No. 5,285,682) addresses the problem of measuring the volume of fluid absorbed in sponges. Ludwigsen (U.S. Pat. No. 5,236,664) addresses the problem of losing blood in non-fluid forms by measuring levels of hemoglobin in blood-containing materials to estimate total blood loss.

The above inventions are useful in solving part of the problem of advising an attending physician about fluid and electrolyte balances in a patient, but the task of tying together the data in real time is left to an attending physician and members of the staff. Due to other demands on the critical attention of these people, attention to the underlying problem of maintaining a proper fluid and electrolyte balance is all too often lacking. None of the above inventions are designed to monitor changes in body electrolyte balance postoperatively. Two of these problems, hyponatremia and hypernatremia, are responsible for in excess of 50,000 deaths in the USA per year.

SUMMARY OF THE INVENTION

Towards solving the problems discussed above, this invention has as an object to present advisory information about a patient's fluid and electrolyte balances, on an at least near-real-time basis, to an attending physician.

The invention provides a digital computer-based system for measuring the fluid volume and, to the extent possible, ionic composition. When direct measurements are not feasible the invention will assist a physician in estimating the ionic composition. Sensors for measuring fluid volume flow and fluid cation or anion levels may be connected to the ingoing and outgoing fluid streams. Alternatively, fluids may be sampled and analyzed in order to determine ionic composition. The invention preferably can also print a history of a patient's fluid and electrolyte status.

Fluids entering into a patient usually have standard parameters for cation or anion concentration, and fully analytic sensors may be replaced by either more cost-effective confirmation sensors (confirming whether the Operating Room technician hung the right bag), by an operator entry, or by bar code.

The exiting fluids (emesis, blood, urine, etc.) have less predictable parameters than the entering fluids. It is therefore advantageous to use analytic sensors on these fluids (as technology allows). Alternatively, fluids may be sampled for analysis. If cation or anion parameter sensors are not available, the system will display a range of historic values for the parameter in question to assist an attending physician, who may then select a value based both upon his or her professional judgment and upon the historical range values.

Fluid inputs and outputs are two factors in maintaining proper fluid and electrolyte values in a patient. A third factor, accounting for which is a further object of the invention, is the baseline parameters of the individual patient. The total body fluid and electrolyte values vary widely among patients depending upon their age, sex, body fat percentage, and weight. However, within a particular group of patients of the same sex, ages, body fat percentages, and weights, the values are predictable. The system of the present invention will thus have a predictor for the total body water and electrolyte values based upon a patient's sex, age, body fat percentage, and weight. In turn the body fat percentage may be estimated by a patient's age, sex, height, and weight, all of which are easily ascertainable. Improved values for body fat percentage may be determined by sensors currently becoming available. Examples of these sensors are triceps skin-fold thickness or bio-impedance measurement devices.

The invention's usefulness extends through preoperative procedures, actual operations, the postoperative care phase, and general patient care.

BRIEF DESCRIPTION OF THE DRAWINGS

FIG. 7 is a table showing compositions of standard intravenous fluids;

FIG. 8 is a table showing electrolyte content for some body fluids;

FIG. 9 shows a representative front panel display for use by an attending physician;

FIG. 11 shows running totals of Total Body Water and total body cation for an example patient through the course of an operation and post-op period.

DETAILED DESCRIPTION OF THE PREFERRED EMBODIMENT

Figure 1:
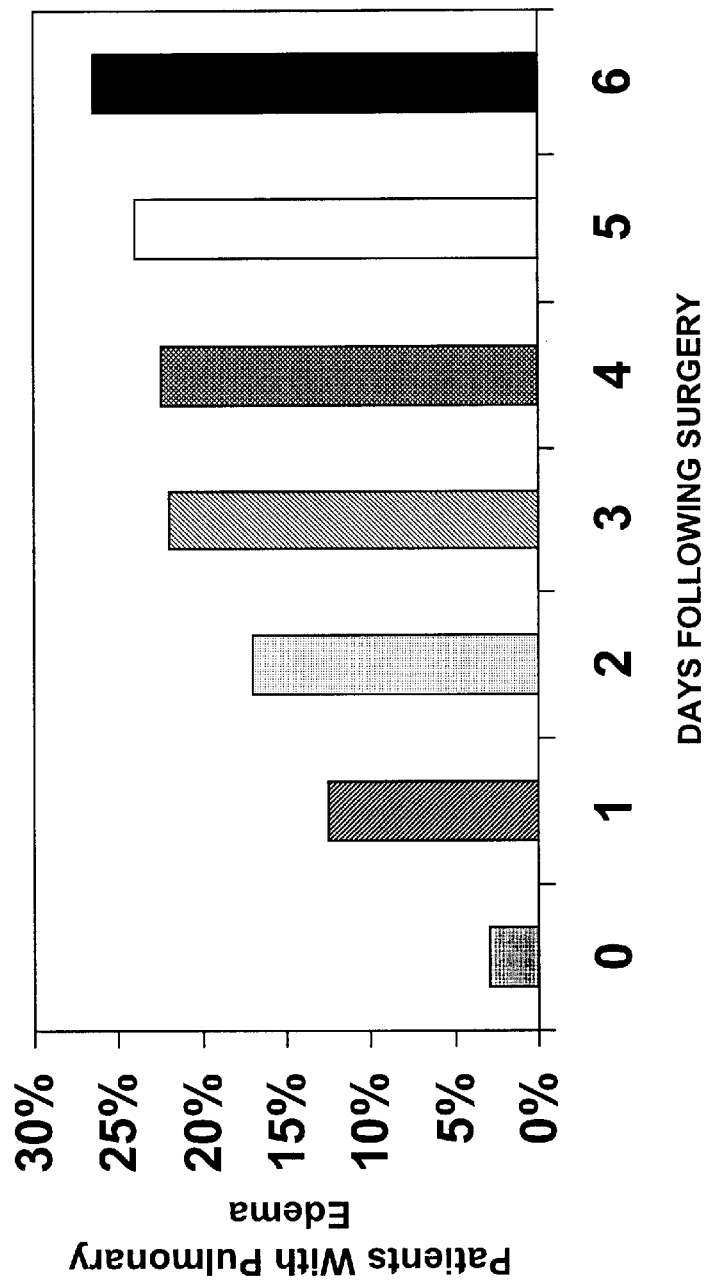
FIG. 1 is a bar chart showing the incidence of postoperative pulmonary edema.
Figure 2:
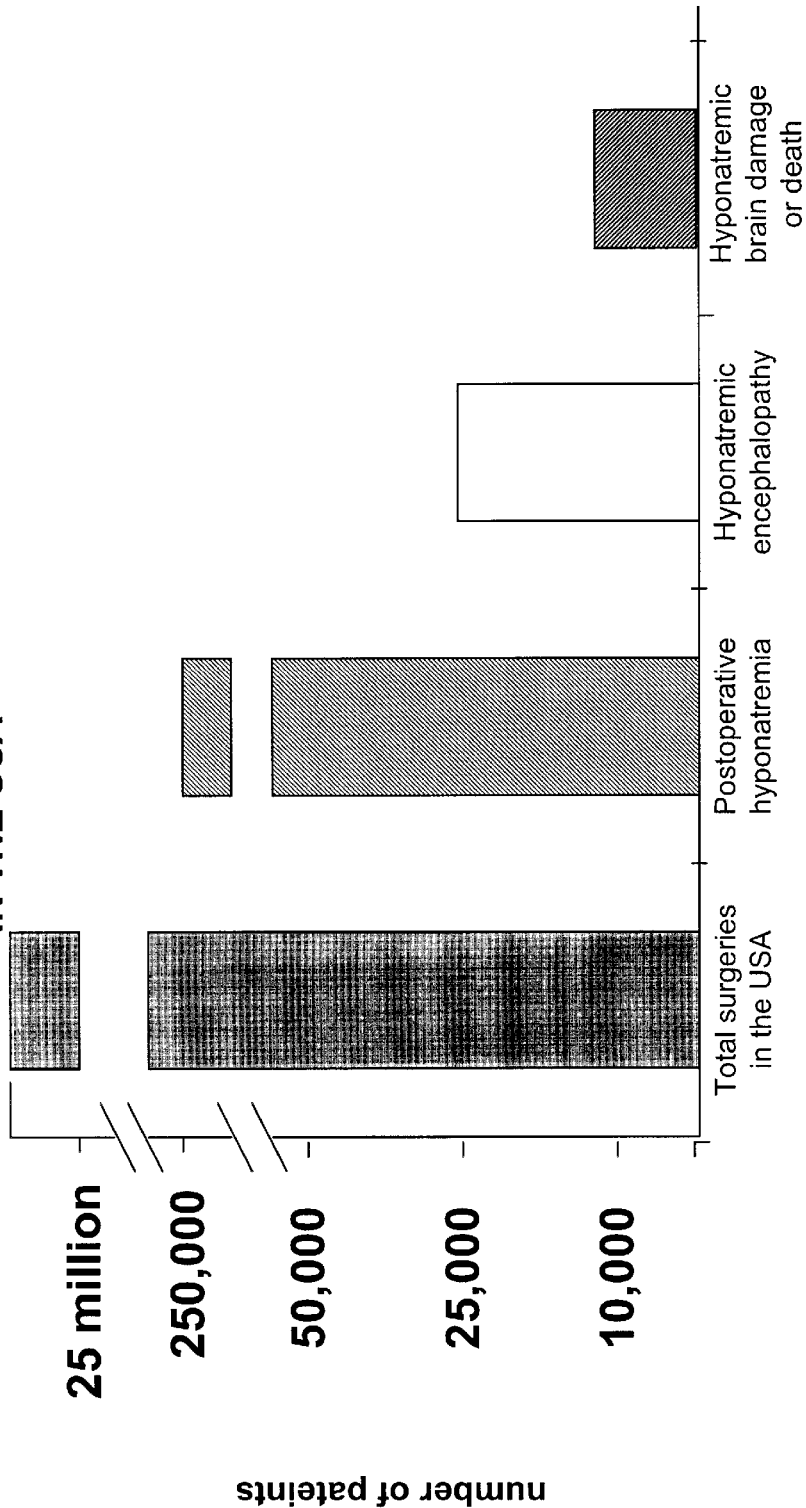
FIG. 2 is a bar chart showing morbidity from hyponatremia.
Figure 3:
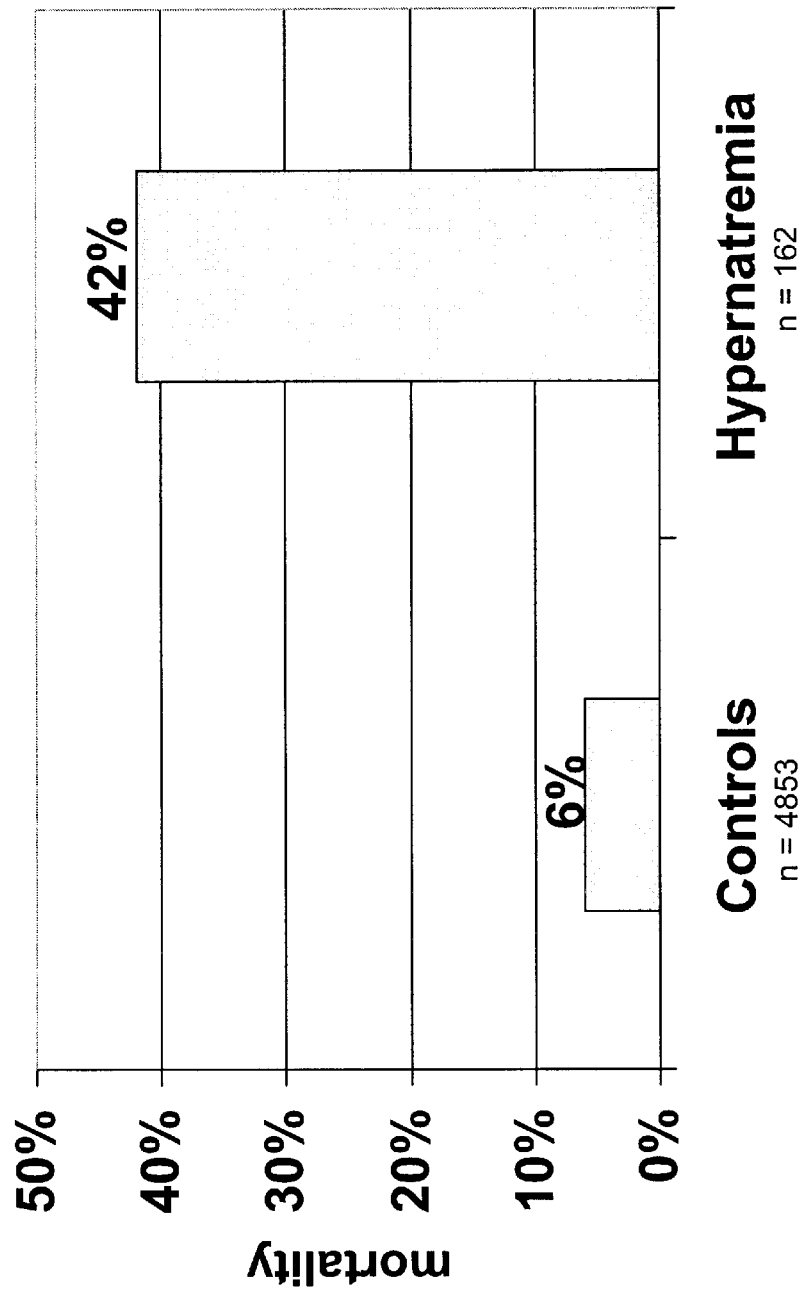
FIG. 3 is a bar chart showing mortality from hypernatremia.
Figure 4:
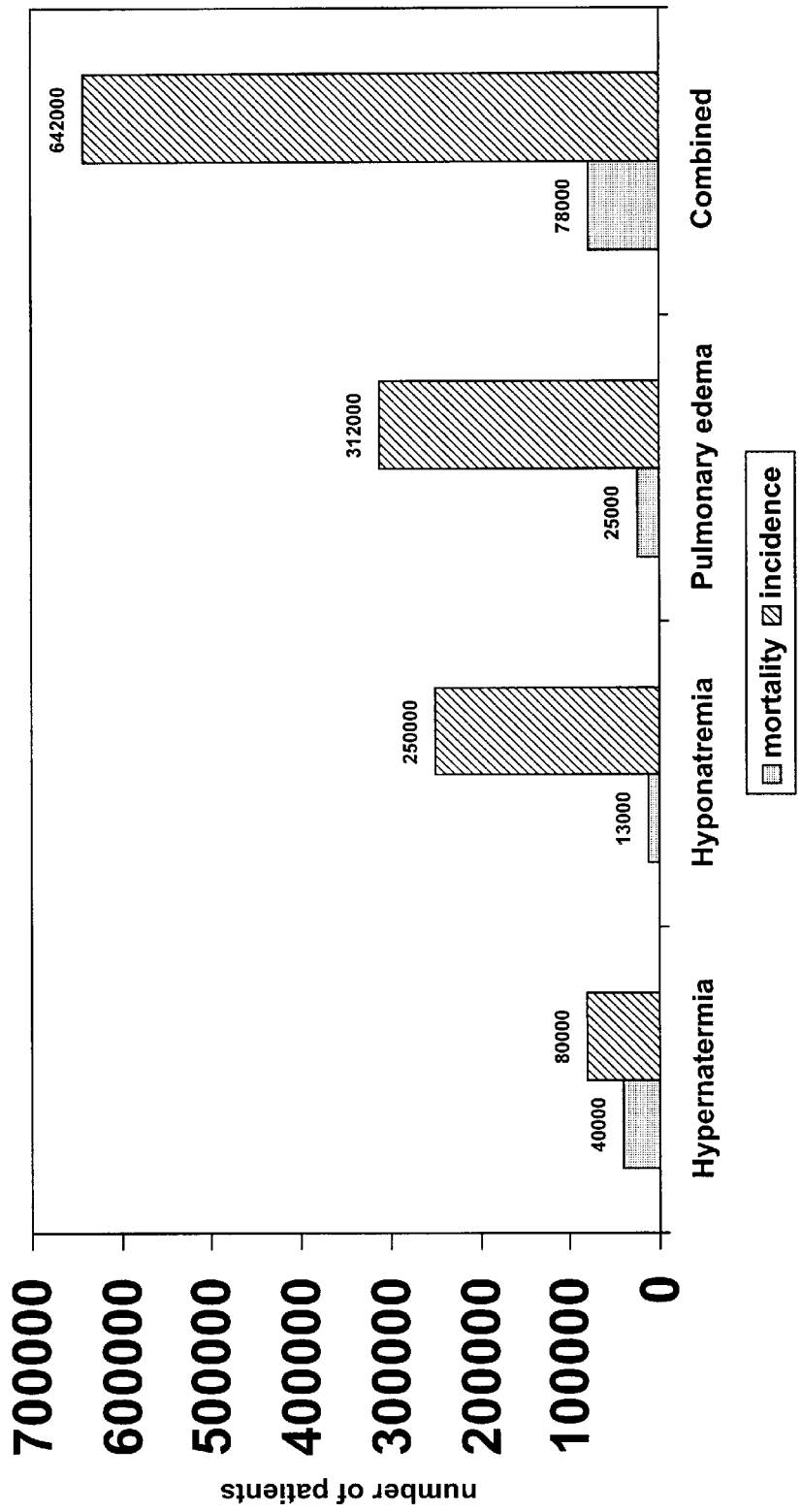
FIG. 4 is a bar chart summarizing postoperative complications.
Figure 5:
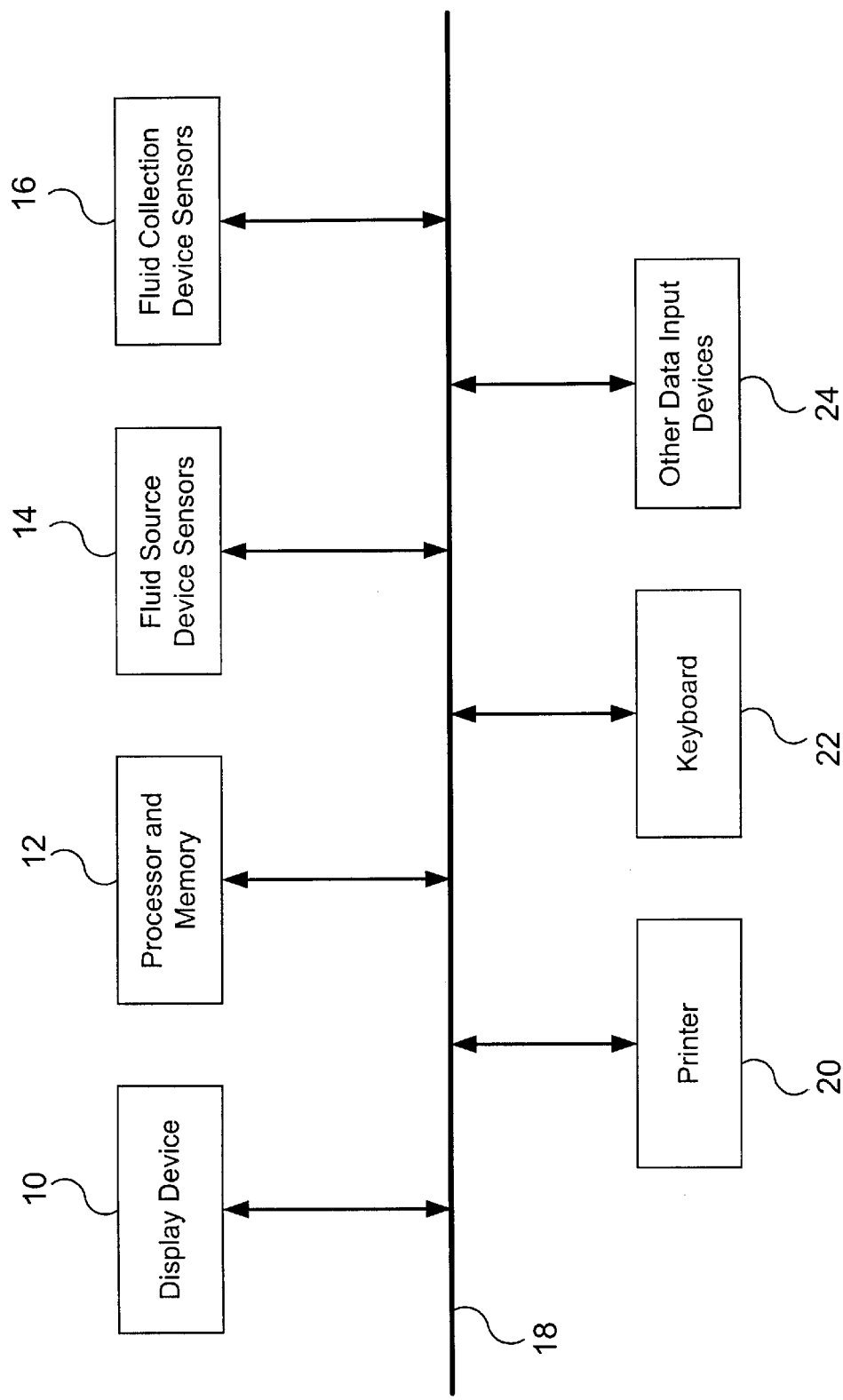
FIG. 5 is a block diagram illustrating components of a fluid and electrolyte balance monitoring system according to the invention.

Referring to FIG. 5 the invention includes a number of fluid source device sensors 14 and a number of fluid collection device sensors 16 each connected via a bus 18 to a digital processor and memory 12. An attending physician inputs additional data through a keyboard 22, and through optional other data input devices 24 such as bar code readers. The attending physician receives information through a display device 10 and through hardcopies printed on a printer 20. The actual configuration of the system and the details of the selection of appropriate sensor technologies depend in part on ongoing cost-benefit analysis as the sensor technologies and prices change over the production lifetime of the system.

Figure 6:
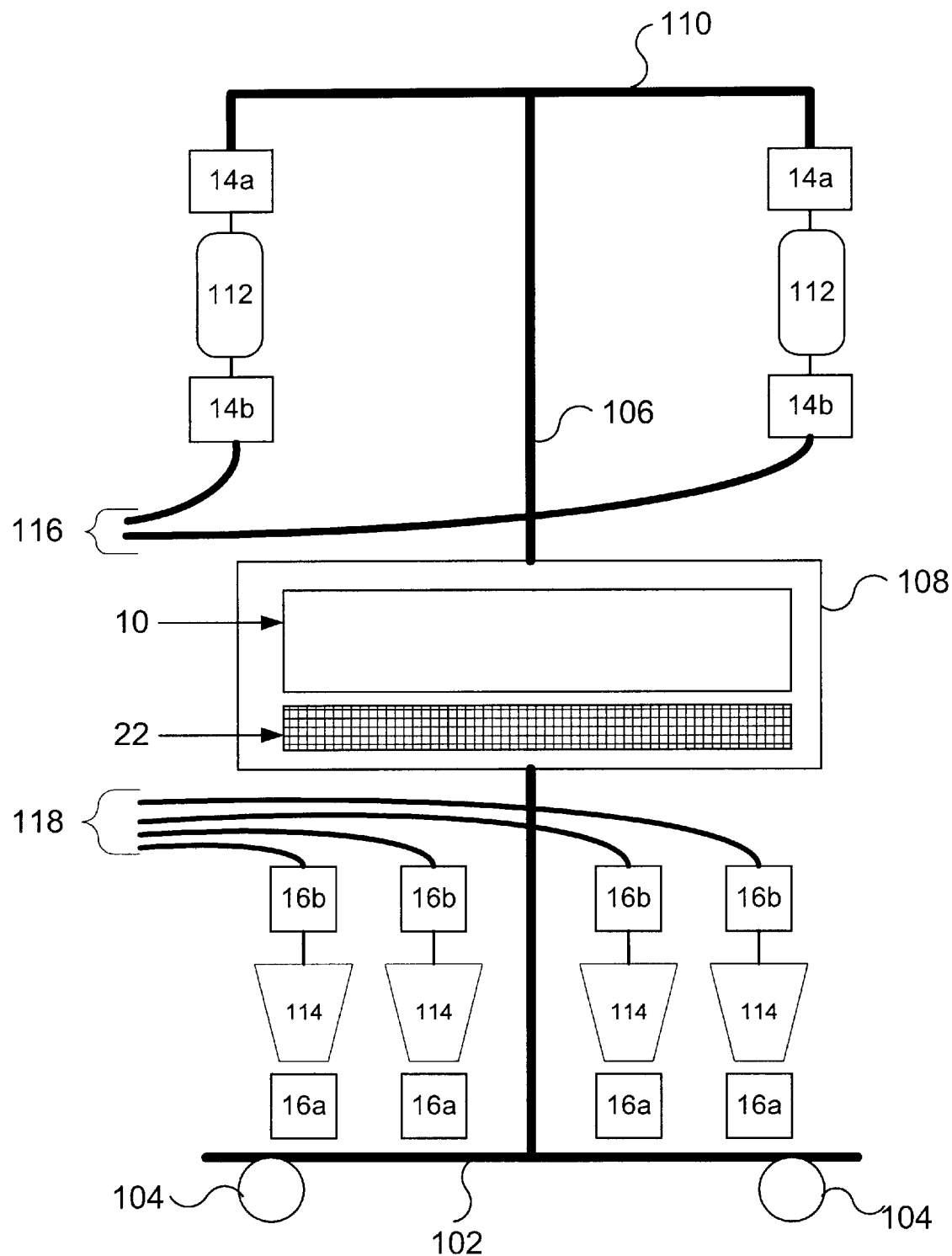
FIG. 6 shows the invention in a preferred embodiment, supported by a pole which facilitates gravity feed and system portability.

FIG. 6 shows several components of the invention in a preferred embodiment used with conventional fluid source devices 112 and fluid collection devices 114 all supported by an IV pole 100. IV pole 100 includes a base 102 mounted on casters 104 to facilitate movement. Mounted on base 102 is a vertical member 106 which supports a computer housing 108 at a height convenient for the attending physician. The housing 108 supports display device 10 and keyboard 22, and also encloses the system processor and memory 12 and provides connection points for optional data input devices 24 such as a bar code reader shown in FIG. 5.

Pole 100 further supports, via a cross member 110, the fluid source containers 112 and fluid source device sensors 14 at a height suitable for gravity feed of the fluids into a patient. Weight scales may be used to sense fluid volumes, although not to sense ion concentrations. If the fluid source device sensors 14 are weight scales, then the fluid source containers 112 rest on or hang from sensors 14a. Otherwise, fluid source device sensors 14b are attached to the output tubing 116 of the fluid source containers 112. The fluid collection containers 114 are supported preferably by the base 102 like the fluid source containers 112. If the fluid collection device sensors 16 are weight scales, then the fluid collection containers 114 rest on or hang from sensors 16a. Otherwise, fluid collection device sensors 16b are attached to input tubing 118 of the fluid collection containers 114.

The fluid source device sensors 14 measure the volume of fluid and the concentration of sodium or of potassium. When the electrolyte concentration is multiplied by the fluid volume, the result yields the total amount of an electrolyte species that is present in the fluid volume.

Several different mechanisms for measuring input fluid volumes are possible: a roller-pump 14b operating at a predetermined flow rate coupled with a timer in the digital computer 12; a scale 14a for continuously weighing the fluid and multiplying the weight by the specific gravity of the fluid to convert the weight to a volume; and in-line fluid flow sensors 14b. These technologies have differing advantages and disadvantages. Since the input fluids are going into a patient, sterility must be maintained. A roller-pump works by squeezing a plastic tube and, since it acts indirectly upon the fluid, sterility may be maintained by disposing of the plastic tubes after one use. However, there may be situations where the fluid should be administered to a patient by gravity feed rather than under pressure. In the case of weighing a fluid to derive its volume, again the determination of the fluid flow is by indirect means and sterility is maintained by using disposable bags and tubing. The use of weight scales also does not require that fluids be administered under pressure. Using in-line fluid flow sensors likewise does not require that fluids be administered under pressure, but has the drawback of requiring the sensors to be sterilized between uses or to be disposable. Roller-pump and in-line fluid flow sensors are typically more expensive and less accurate: therefore, the invention in the preferred embodiment uses weight scales.

The most commonly used postoperative fluids are described in FIG. 7. Determining the cation or anion concentrations of the various input fluids is simplified by the fact that the dozen or so typically administered fluids are manufactured or selected to have standard properties and to include standard amounts of the cations and anions essential to monitor: Sodium (Na+), Potassium (K+), and Chloride (Cl−). The cation or anion concentrations in the administered fluids may be determined in any of three different ways: 1) by the use of highly accurate analytic sensors; 2) by the use of confirmation sensors which only need a level of accuracy sufficient to confirm the parameters of the selected fluid; or 3) by attending physician entry in reliance on the labeling of the fluid bags. Loss of Magnesium (Mg++) from the body is also important to estimate but is generally not in any standard fluid that is administered.

Each of these methods has advantages and disadvantages. There are two times when errors can be made in the cation and anion concentration of a fluid: first when the fluid is prepared by the fluid manufacturer and put into a labeled bag, and second when an OR technician hangs the bag in preparation for its administration to a patient. The use of analytic sensors can detect both kinds of errors, but at a cost of complexity and the need for recurring calibration. Again, these sensors risk low reliability due to the need for sterility and autoclaving. The use of less costly confirmation sensors (osmolarity, chloride conductivity) only allows the detection of gross errors at the time of use of the fluid, and does not detect errors made during the manufacture of the fluid bag. However, it has been found that in the administration of fluids the overwhelming majority of errors, numerically still rare, arise from an OR technician hanging the wrong bag of fluid. The use of confirmation sensors adds a reasonable level of protection against this eventuality without unreasonably increasing the complexity and cost of an IV system. In any case, manual or manually assisted entry of data concerning input fluid factors is adequate. A physician directing the administration of a fluid can enter the short name of the fluid or press an appropriate function key at the system keyboard 22, and the digital computer 12 then looks-up cation or anion concentration values from a table. Alternately a physician can use a manually assisted data entry device such as a bar-code wand to enter cation or anion concentration values.

Monitoring the output fluids presents different problems than monitoring the input fluids. Since the fluids are leaving a patient, the sterility of system components is not an issue, but the requirements for sensors are greater due to the non-standard nature of the output fluids. The output fluids needing to be monitored include:

1) emesis (vomit)
2) gastric drainage
3) chest tube drainage
4) laparoscopy drainage
5) diarrhea
6) biliary drainage
7) urine
8) thirds pace loss
9) blood A series of receiving containers 114 captures the volumes of these fluids. There are several technologies available for determining the volumes. A weight scale is a reasonable technology. The volumes of fluids in the receiving containers can also be measured by using sound or an interrupted light beam to determine the free air space left in a container 114.

There are several kinds of output fluids which will defy analytic measurement but cannot be ignored. The most important ones are the third space fluids and the blood residing in or on lap sponges and other surgical implements. An attending physician will need to estimate the third space losses and manually enter the values into the system. Lap sponges can be weighed and the dry weight of the sponges subtracted to find the weight of the blood alone, which can then be converted to volume by using the specific gravity of whole blood as a best estimate.

The concentrations of cations and anions in each of these fluids varies between patients. Averages and ranges for some of these are given in FIG. 8. One method of measuring these concentrations, which could be used presently, applies techniques from analytical chemistry to accurately measure the amount of different electrolytes that are present. Samples can be removed from the receiving containers and sent to a laboratory. However, this entails additional cost and delay and in clinical practice is almost never done. Sensors can be used instead of a laboratory. Currently available suitable sensors include ion specific electrodes, optical spectrometers, and sensors which directly measure electrical properties of a fluid. This technique would be the most accurate but has practical problems associated with the availability of reasonably priced sensors. The use of low accuracy "confirmation" sensors, which might be sufficient to identify the type of fluid being administered from the handful of known fluids used in IV therapy, would not be sufficient to identify the electrolyte concentrations in the fluids being collected, which would be much more variable.

An alternative approach, if sensors are too expensive, is to use "known" average values obtained from the medical literature or from studies of patients. If in addition, ranges for the electrolyte concentrations are "known," then ranges for the amount of the electrolyte present in the fluid can be computed. Note that the electrolyte concentrations of the fluids being administered are already known if the type of fluid being administered is known. In this way the system can present an attending physician with average values and a standard deviation of cation and anion concentrations in the output fluid in question. The physician can then exercise his or her professional judgment and select a tailored value close to the average which the system will use in conjunction with the measured volumes of the fluids.

A fourth method combines benefits of two or more confirmation sensor methods. One measure of the amount of various substances dissolved in a fluid is known as the osmolarity of the fluid. Osmolarity can be measured using a variety of techniques including the measurement of osmotic pressure and a method known as the freezing point depression technique which relies on the principle that the freezing point of water is depressed by 0.00186° C. per milli-osmol (mOsm) when dissolved substances are present. It would seem that the measurement of osmolarity can be made more easily than the measurement of individual electrolyte concentrations in a complex fluid that contains several dissolved substances.

If in addition to measuring the osmolarity, the overall electrical conductivity of the fluid that is collected from the body is measured (not ion-specific), then these two pieces of information, in conjunction with the known fluid type, i.e. urine, blood, gastric drainage, etc. should allow a better estimate of the individual electrolyte concentrations.
ex: Saline solution at 70 mM/liter:

If the NaCl is completely ionized, there are two ions, Na+ and Cl− for each molecule of NaCl. This means that the osmolarity of the solution is 140 mOsm/liter. The freezing point depression would be 0.2604° C. The solution is also electrically conductive.
ex: Urine Urine composition is approximately 50% urea and 25% NaCl. One could use the known concentrations along with electrical conductivity to make estimates of the Na+concentration.

One could add other measurements, i.e. color, pH, etc. to have an even better measurement of electrolyte concentration. One way to do this would be to develop a data base by taking these measurements on a number of fluid samples and then using curve fitting, pattern recognition or other techniques such as neural networks to develop a relationship between the measurement data that are available and the desired measurements, i.e. electrolyte concentrations. Special sensors can be developed, such as a combined freezing point depression and electrical conductivity sensor, or a freezing point depression and color sensor.

The invention in a preferred embodiment has a display device 10 as shown schematically in FIG. 5 which gives to an attending physician a readout as shown in a typical view in FIG. 9. The display device 10 can be either a Cathode Ray Tube (CRT) display, a gaseous plasma display, or a Liquid Crystal Display (LCD). The preferred embodiment uses an LCD display, as these devices' thinness allows mounting them on the housing 108 immediately above keyboard 22. When patient care is initiated, an attending physician scrolls through the entry fields displayed on display device 10 and enters values from a patient's medical records. Other fields are controlled by digital processor 12, either through interpreting sensor data or through the intervention of an attending physician. Such intervention may be because of a direction to administer a given fluid (e.g. give 1 liter of NS) or when the physician must manually enter estimated fluid parameters for those outgoing fluids which cannot be analyzed automatically. In the later case the physician will enter the generic outgoing fluid type (e.g. urine) and receive displayed historic values for the average and standard deviation of that fluid's cation and anion concentration. The physician will then select the value that he or she believes to be the best approximation for a particular patient.

The preferred embodiment has a keyboard for the attending physician to enter data. Since there are only a dozen input fluids in wide use and only about 10 outgoing fluids which require tracking, individual function keys preferably are assigned to each type of fluid. Additional alphanumeric keys allow entering unusual fluid types and the numeric input of data as described above.

A digital processor and memory are shown in the system block diagram of FIG. 5. The digital processor and memory will be located in the system housing which houses the display device and keyboard. Because the processing capacity requirements are relatively slight, this may be a relatively low powered microprocessor or microcontroller.

The preferred embodiment also includes a printer 20 or other hardcopy device attached to the system bus 18 as shown in FIG. 5. The output device can be mounted almost anywhere within a reasonable distance from computer housing 108, but is preferably mounted on the side of the housing 108 opposite the display device 10 and keyboard 22. For clinical use, histories will be printed on standard (8.5 by 11 inch) sized sheets of paper.

Up until this time measurements of the volumes and cation or anion concentrations of the input and output fluids have been discussed. It is also necessary to produce a baseline for the fluids in a patient. The system uses look-up tables to estimate a patient's total body water (TBW) and electrolyte content. The system display 10 displays prompts to an attending physician, who then enters values for a patient's age, sex, height, and weight. The system then calculates a derived value for percentage body fat (body mass index (BMI)) using the formula BMI=(patient's weight in Kg/(patient's height in cm)$^2$)

and uses this value in conjunction with the other entries to derive the patient's total body water and electrolyte content. The following simplified list illustrates such a look-up table:

| Age | Male | Female |
|---|---|---|
| 10–18 | 59 | 57 |
| 18–40 | 61 | 51 |
| 40–60 | 55 | 47 |
| over 60 | 52 | 46 |
| obese & over 60 | 45 | 40 |

More accurate values for percentages of body fat may be obtained by various tests, instruments, and sensors. It is likely that the commercially produced version of the invention will utilize one of these measured values. One such instrument is the inch triceps, which pinches a skin fold on a patient's upper arm and gives an improved value for percentage body fat compared to the body mass index as calculated above. A laboratory test for tritium content in a patient's blood also yields an improved value for percentage body fat. A recently developed special scale upon which a patient stands barefoot uses bioimpedance measurements to give a direct digital value for percentage body fat. However, even when the above measurements cannot be made (e.g. a patient has burns preventing use of the inch triceps) estimates based upon age, sex, height, and weight are always available.

Figure 10:
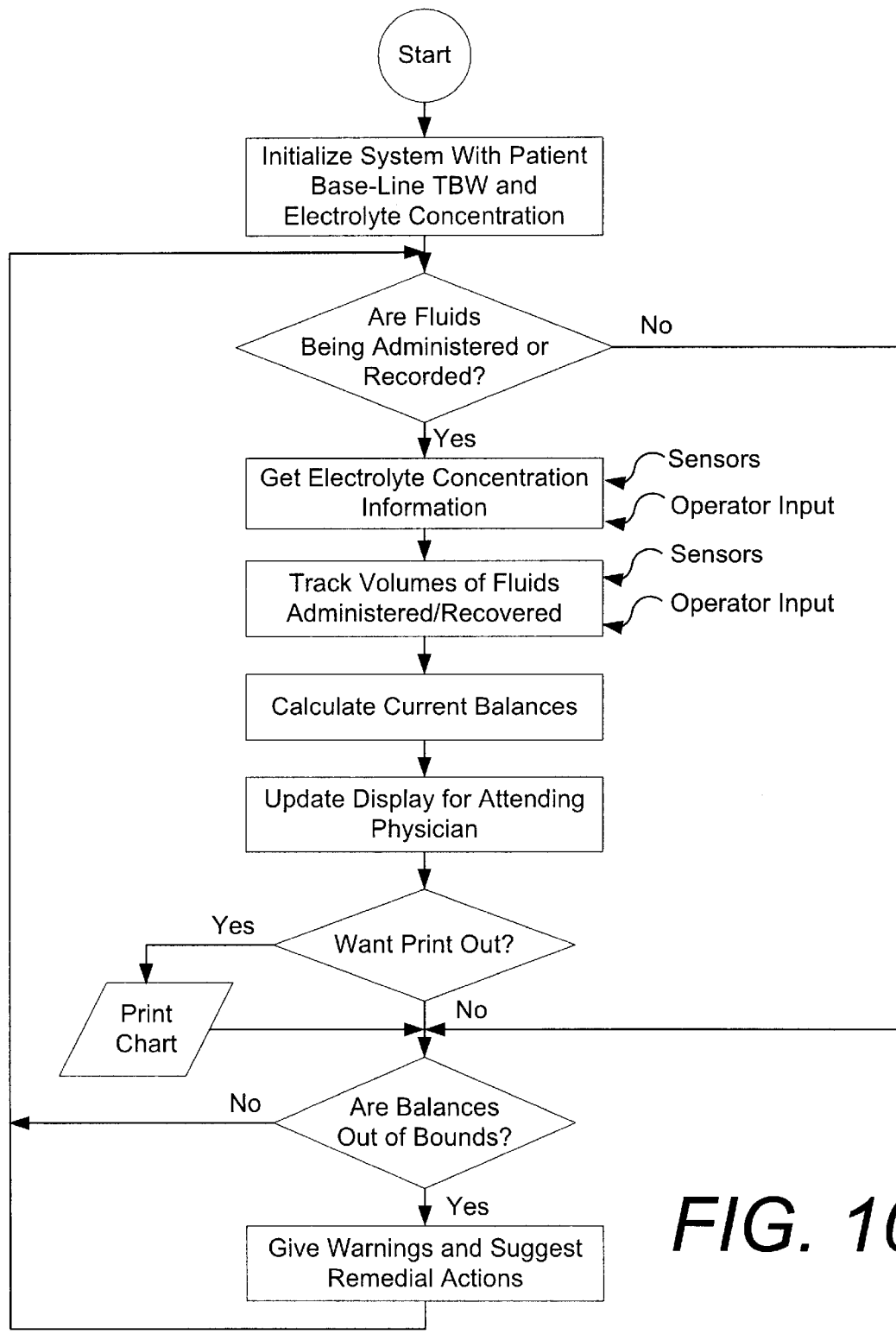
FIG. 10 shows a representative process flowchart describing the monitoring functions of the invention.

As shown in the flowchart of FIG. 10, once the system contains baseline information about the patient's TBW and cation or anion concentration, the system enters its monitoring mode. The software continuously monitors the input and output fluids from the patient for volume and cation or anion concentration. In some cases the monitoring will be fully automatic while in other cases an attending physician will intervene. In the preferred embodiment of the invention, when it is necessary to administer fluids to a patient the attending physician directs the OR technician to hang the appropriate plastic bag 112 of fluid from the cross member 110 and then connect this via IV tubes 116 to the patient. Depending upon the precise implementation of the invention, the attending physician enters information about the fluid bag 112 manually via the keyboard 22 or semi-automatically via a bar code reader 24. The system software first checks the entered values of the cation or anion concentrations by comparing them with the signals from the ion concentration sensor (if available), and then continuously monitors the amount of fluid given using the weight scale or fluid flow sensor 14. This allows for near-real-time calculations of the patient's current fluid and electrolyte balance values. These values are compared with boundary values beyond which the patient may exhibit pathology.

Fluids leaving the patient are tracked in a similar manner. As an example, a urinary catheter is attached via tubing to a fluid output container 114 at the base 102 of the invention. The attending physician indicates that fluid to be monitored is urine, and the system displays the mean and standard deviation of cation and anion concentrations in urine. The attending physician then enters cation and anion concentration values corresponding to the patient's condition (e.g. the urine from a dehydrated patient has above-normal concentrations of Na+). The system will again continuously monitor the volume of the fluid and again update in near-real-time the patient's fluid and electrolyte balance values.

If the system ever detects a value of the patient's fluid and electrolyte balances which is out of permissible bounds, it uses visual (flashing lights) and audible (tone) signals to attract the attention of the attending physician. The display will show exactly what the problem is and suggest corrective fluid application.

Hypothetical Patient:

A 30-year-old woman patient weighs 127 lbs. (58 kg). From the literature, her total body water (TBW) is found to be 28 liters. Prior to an operation, her plasma Na is 138 mmol/L, K is 4.0 mmol/L, and hematocrit is 40%.

The patient then has a gastric resection surgery for ulcer disease, during which she receives 4 liters (4000 ml) of Ringers lactate and loses an estimated 1800 ml. of blood.

During the initial 24 hours post-operatively she is given 2000 ml of 280 mmol/L glucose in water (5% dextrose in water) intravenously, which has no electrolyte. Postoperatively, she loses 3.6 liters of gastric suction and 3.1 liters of urine. After the initial 24 hours, her plasma Na is 136 mmol/L and K is 3.6 mmol/L.

What is the patient's fluid status at the end of the initial 24 hours; and what should be done? The balance data is summarized in FIG. 11.

Prior to surgery, her balance was:

28 liters of total body water (48% of body weight)

Total body cation (Na+K)=28 L×138 mmol/L=3864 mmoles.

Immediately after surgery, her balance was 30.2 liters water and 4144 mmoles cation Thus, after the initial 24 hours, the net fluid and electrolyte balance shows a deficit of 2.5 liters water and a deficit of 384 mmoles cation. This can be repaired with 2.5 liters intravenously of isotonic saline (154 mM NaCl).

The exemplary embodiments described herein are for purposes of illustration and are not intended to be limiting. Therefore, those skilled in the art will recognize that other embodiments could be practiced without departing from the scope and spirit of the claims set forth below.

What is claimed is:

1. A fluid and electrolyte balance monitoring system, comprising:

input fluid measuring means for measuring a volume of fluid entering a patient;

input fluid analyzing means for determining electrolyte parameters of fluid entering the patient;

output fluid measuring means for measuring a volume of fluid exiting the patient;

output fluid analyzing means for determining electrolyte parameters of fluid exiting the patient; and fluid volume and electrolyte tracking means for calculating and monitoring a fluid volume status and an electrolyte status of the patient based on information obtained from said input fluid measuring means, said input fluid analyzing means, said output fluid measuring means, and said output fluid analyzing means.

2. The system of claim 1 wherein the input fluid measuring means comprises a plurality of roller pumps with adjustable flow rates.

3. The system of claim 1 wherein the input fluid measuring means weighs input fluids.

4. The system of claim 1 wherein the input fluid measuring means comprises at least one in-line flow meter.

5. The system of claim 1 wherein the input fluid analyzing means comprises a plurality of analytic sensors.

6. The system f claim 5 wherein the input fluid analyzing means further comprises a plurality of confirmation sensors.

7. The system of claim 1 wherein the input fluid analyzing means allows manual entry of an amount of electrolytes entering the patient by an operator.

8. The system of claim 1 wherein the output fluid measuring means weighs output fluids.

9. The system of claim 1 wherein the output fluid measuring means comprises at least one means for measuring the height of a fluid in a standard container.

10. The system of claim 1 wherein the output fluid measuring means comprises at least one acoustic sensor for directly measuring volumes of fluids in standard containers.

11. The system of claim 1 wherein the output fluid analyzing means comprises at least one analytic sensor connected to the output fluids.

12. The system of claim 1 wherein the output fluid analyzing means measures osmolarity.

13. The system of claim as in claim 12 wherein the output fluid analyzing means further combines a measured osmolarity with a measured electrical conductivity, in conjunction with a known fluid type to determine electrolyte concentrations.

14. The system of claim 1 wherein the output fluid analyzing means includes medical historical value ranges for analogous fluids.

15. The system of claim 1 wherein the fluid volume and electrolyte tracking means comprises means for determining a present status of the patient's body water volume.

16. The system of claim 15 wherein the means for determining a present status of the patient's body water volume uses approximations calculated from a patient's age, height, weight, and sex.

17. The system of claim 15 wherein the means for determining a present status of the patient's body water volume comprise a tritium content sensor.

18. The system of claim 15 wherein the means for determining a present status of the patient's body water volume comprise inch triceps.

19. The system of claim 15 wherein the means for determining a present status of the patient's body water volume utilizes bioimpedance measurements.

20. The system of claim 1 wherein said fluid volume and electrolyte tracking means provides an advisory warning signal if the fluid volume status of the patient goes outside a range of predetermined values.

21. The system of claim 1 wherein said fluid volume and electrolyte tracking means provides an advisory warning signal if the electrolyte status of the patient goes outside a range of predetermined values.

22. The system of claim 1 wherein said fluid volume and electrolyte tracking means, based on the fluid volume status and the electrolyte status of the patient, suggests the application of corrective fluids to the patient.

23. The system of claim 1 wherein said fluid volume and electrolyte tracking means, based on the fluid volume status and the electrolyte status of the patient, automatically controls a rate of corrective fluid input to the patient.

24. The system of claim 1 further including a baseline input means for entering initial baseline information about the patient, wherein said fluid volume status and said electrolyte status of the patient is also based on information obtained from said baseline input means.

25. An electrolyte balance monitoring system, comprising:

input fluid analyzing means for determining electrolyte parameters of fluid entering the patient;

output fluid analyzing means for determining electrolyte parameters of fluid exiting the patient; and electrolyte tracking means for calculating and monitoring an electrolyte status of the patient based on information obtained from said input fluid analyzing means, and said output fluid analyzing means.

26. The system of claim 25, wherein said electrolyte tracking means provides an advisory warning signal if the electrolyte status of the patient goes outside a range of predetermined values.

27. The system of claim 25, wherein said electrolyte tracking means, based on the electrolyte status of the patient, suggests the application of corrective electrolytes to the patient.

28. The system of claim 25, wherein said electrolyte tracking means, based on the electrolyte status of the patient, automatically controls a rate of corrective electrolyte input to the patient.

29. The system of claim 25, further including a baseline input means for entering initial baseline information about the patient, wherein said electrolyte status of the patient is also based on information obtained from said baseline input means.

* * * * *